(12) United States Patent  
Shukla et al.

(10) Patent No.: US 8,034,239 B2  
(45) Date of Patent: Oct. 11, 2011

(54) DEVICE FOR SAMPLE PREPARATION

(76) Inventors: Ashok K. Shukla, Elliott City, MD (US); Mukta Shukla, Ellicott City, MD (US)

( * ) Notice: Subject to any disclaimer, the term of this patent is extended or adjusted under 35 U.S.C. 154(b) by 945 days.

(21) Appl. No.: 11/985,517

(22) Filed: Nov. 15, 2007

(65) Prior Publication Data

US 2008/0128365 A1 Jun. 5, 2008

Related U.S. Application Data (60) Provisional application No. 60/858,872, filed on Nov. 15, 2006.

(51) Int. Cl.
*B01D 15/08* (2006.01)

(52) U.S. Cl. ............. 210/198.2; 210/635; 210/656; 422/70; 422/525

(58) Field of Classification Search ........... 210/635, 210/656, 198.2, 289, 291, 497.1, 497.3, 485, 210/498; 422/70, 525, 527, 535
See application file for complete search history.

(56) References Cited

U.S. PATENT DOCUMENTS

| | | | | | |
|---|---|---|---|---|---|
| 1,840,053 | A | * | 1/1932 | Seymour | 53/436 |
| 2,049,225 | A | * | 7/1936 | Ripley | 384/171 |
| 3,478,886 | A | * | 11/1969 | Hornbeck | 210/198.2 |
| 4,187,724 | A | * | 2/1980 | Citrin | 73/864.14 |
| 4,369,665 | A | * | 1/1983 | Citrin | 73/864.18 |
| 4,934,272 | A | * | 6/1990 | Sternin et al. | 102/334 |
| 6,190,559 | B1 | * | 2/2001 | Valaskovic | 210/656 |
| 6,537,502 | B1 | * | 3/2003 | Shukla et al. | 422/526 |
| 7,276,158 | B1 | * | 10/2007 | Shukla et al. | 210/198.2 |
| 2002/0162655 | A1 | * | 11/2002 | Lynde et al. | 166/99 |

* cited by examiner

*Primary Examiner* — Ernest G Therkorn (57) ABSTRACT

This invention relates to a pipette tip or tube designed to perform biological or chemical sample preparation, purification or separation. The narrow end of the pipette tip is twisted in such a way that it forms a narrow spiral passage, which allows the retention of the chromatographic material in the pipette tip. The narrow spiral formed by twisting the capillary or the tube creates an opening that is large enough to permit the passage of fluids or smaller particles, but small enough to block the passage of solid materials or larger particles, The device described herein can be used for sample separation or purification using a vacuum, pressure, centrifugation, gravitation or other separation methods.

13 Claims, 8 Drawing Sheets

DEVICE FOR SAMPLE PREPARATION

Priority date provisional Application No. 60/858,872 filed on Nov. 15, 2006.

FIELD OF THE INVENTION

This invention relates to a pipette tip or tube designed to perform biological or chemical sample preparation, purification or separation. The narrow end of the pipette tip is twisted in such a way that it forms a narrow spiral passage, which allows the retention of the chromatographic material in the pipette tip. The narrow spiral formed by twisting the capillary or the tube creates an opening that is large enough to permit the passage of fluids or smaller particles, but small enough to block the passage of solid materials or larger particles, such as those comprising chromatography media. Such a device can thus be used for the filtration or separation of samples without the use of a filter, secondary solid matrix or any other components needed to hold chromatography media and other solid matrices within the pipette tip during the separation process. The device described herein can be used for sample separation or purification using a vacuum, pressure, centrifugation, gravitation or other separation methods.

BACKGROUND OF INVENTION

Tube: means capillary, tube, pipette tip, with any geometry of hole such as round, square, cylindrical, triangular, elliptical, parabolic or any shape which can be in the form of a tube. Internal diameter of the tube is from 0.001-25 mm. The length of the tube can be from 0.1-10000 mm.

Narrow Spiral Opening: means that the tube or capillary is twisted along the length of the tube in such a way that one end is fixed and other end (rotating end) is twisted with force at any given angle to form a spiral shape. The center of the spiral can be at any place between the two ends of the tube. During the twisting process, the length of the tube can be changed or unchanged depending on the application.

Spiral shape is created by twisting the tube at any angle from 1 degree to 360 degree or multiple turns of an angle between 1-360 degree.

Chromatographic material means, the regular, irregular, spherical, broken particles of silica, metal, polymers, metal oxides, non-metal oxides. These particles can be porous or nonporous. The pore size can be from 20-40000 nm. These particles can be modified chemically, physically, mechanically or by affinity media. The size of the particles can be from 0.001-1 mm.

Although a spectrum of analytical methods for small sample separation and purification have been developed, a number of problems, such as the slow speed of the separation process and the loss of sample volumes, limit the quality of currently available methods.

In this invention, we describe the use of a tube such as pipette tip, which has a spiral narrow opening at the lower end of the tip, designed for sample filtration or separation. The spiral narrow opening is of such dimensions that fluids and smaller particles can pass through the lower end while larger particles are retained. The application of such a device is useful for performing sample separation and filtration with chromatography and other separation media because it eliminates the need to place a filter or secondary solid matrices into the tip to retain said chromatography and other separation media within the tip during sample preparation. Depending on the specifications of the chromatography material, selected molecules from the sample can be separated or purified by binding to, or by being entrapped into the said material. The bound molecules can later be eluted from the said material by the use of different solvents.

Filters and secondary solid matrices are traditionally used in separation columns such as pipette tips to retain the solid matrix or column material in the container, while letting fluids and desired sample components flow through. Currently available sample preparation pipette tips rely on filters and solid matrices to hold chromatography and separation media in the tip while permitting selective components of the sample to pass through the lower end of the tip. The filters used in such devices may be made of silica, polypropylene, nylon, polytetrafluoroethylene or any other inert materials that do not react with the elution solution. The pore size of the filter material should be smaller than the particle size of the solid matrix or chromatography material placed above it so that the solid matrix or chromatography material is retained in the tip.

In pipette tips or other separation columns using filters, sample separation can be performed by centrifugation, gravitation, and vacuum suction, pressure application or by syringe- or pipette-based sample delivery through the tip or column. Such devices are used for the separation and purification of small sample volumes of bio-molecules such as proteins, peptides and DNA. The solid matrix or column material can consist of any material such as gel-filtration, affinity, ion-exchange, reverse-phase, and silica or modified-silica materials.

When sample volumes in the micro liter range are separated using currently available pipette tips and other separation/chromatography columns, one of the commonly associated problems is sample loss during the separation process due to retention of the sample on the filter or within the secondary solid matrices. Since the concentration of bio-molecules in micro volume samples is very small, the retention of molecules in the filter or secondary solid matrix can result in significant loss of the total sample volume. Also, since the volume of the filter or secondary solid matrix is often as large as the volume of the micro volume sample itself, the separation or chromatography process is adversely affected due to the large volume of filter material through which the sample must pass during the separation process. The filter material may also absorb proteins or bio-molecules from the sample, resulting in lower than desirable sample recovery.

Also, the filter material and solid matrix or column material may behave differently in different elution media, subsequently interfering with both the quality of the separation process and the volume of the sample retained. Furthermore, the presence of the filter material also slows down the sample separation process because the sample is first passed through the column material and then the filter prior to the completion of sample separation. Additionally, the structure and design of many micro-pipette tips, designed for micro-liter sample volumes, is not well suited for the addition of filters or secondary solid matrices into the tip.

The invention described and claimed herein comprises a tube or pipette tip designed to perform filtration or sample separation on the basis of a narrow spiral opening in the tip for sample filtration or separation. The narrow spiral opening is of such dimensions that fluids and smaller particles can pass through while larger particles are retained in the tip. During the process of sample separation, performed by centrifugation, gravitation, vacuum suction, pressure application or by syringe-based sample delivery through the container described herein, the filter solid matrix or column material will be retained in the tip while the sample will pass through.

The features of the present invention eliminate the need for filters or secondary solid matrices at the bottom of the tip to support the chromatography material during sample separation. Thus, the present invention, as described herein, will result in higher sample recovery due to the lack of sample retention on the filter or secondary solid matrix. The present invention will also eliminate separation problems associated with filter-materials and secondary solid matrices interacting differently with alternate elution media, thus improving the quality of the separation. The present invention also leads to more rapid sample separation since the sample does not flow through a filter or secondary solid matrices as part of the separation process.

The various features of novelty, which characterize the invention, are pointed out with particularity in the claims annexed to and forming a part of this disclosure. For a better understanding of the invention, its advantages and objects, reference is made to the accompanying drawings and descriptive matter in which a preferred embodiment of the invention is illustrated.

BRIEF DESCRIPTION OF THE DRAWINGS

The foregoing and still other objects of this invention will become apparent, along with various advantages and features of novelty residing in the present embodiments, from study of the following drawings, in which.

DESCRIPTION OF THE PREFERRED EMBODIMENTS

Figure 1:
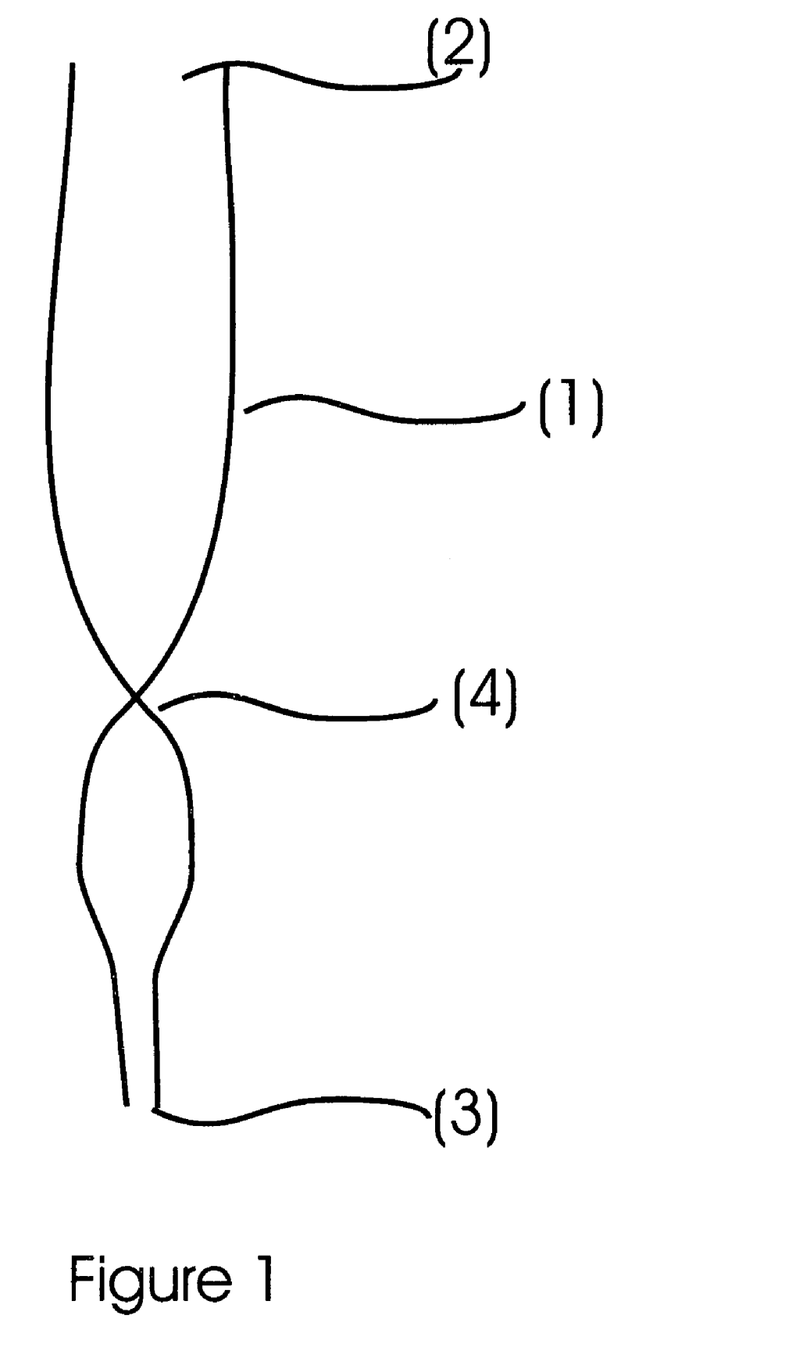
FIG. 1 is an expanded view of one embodiment of the pipette tip, according to the present invention.

Referring to the drawings, FIG. 1 is an expanded view of one embodiment of the pipette tip or a tube (1), according to the present invention. The internal diameter of the tube can be from 0.001-25 mm. The pipette tip (1), has an upper end (2) and a lower end (3). The lower end contains a spiral opening (4) designed to permit the selective passage of smaller particles or fluids through said spiral opening (4) while retaining larger particles in said tip (1). Said pipette tip (1) can be any type of holding unit such as a tube, housing, column, vial or any other type of holding unit suited to the sample preparation process. Said pipette tip (1) can be of any shape or size and both the upper end (2) and lower end (3) may be closed or open ends. The tube can be straight, tapered or any other geometry. Said pipette tip (1) can be made of one or more materials including but not limited to polytetrafluoroethylene, polysulfone, polyethersulfone, cellulose acetate, polystyrene, polystyrene/acrylonitrile copolymer, PVDF, metal and glass. Said pipette tip (tube) (1) can have a volume anywhere from 0.0001 to 100 milliliters.

Figure 2:
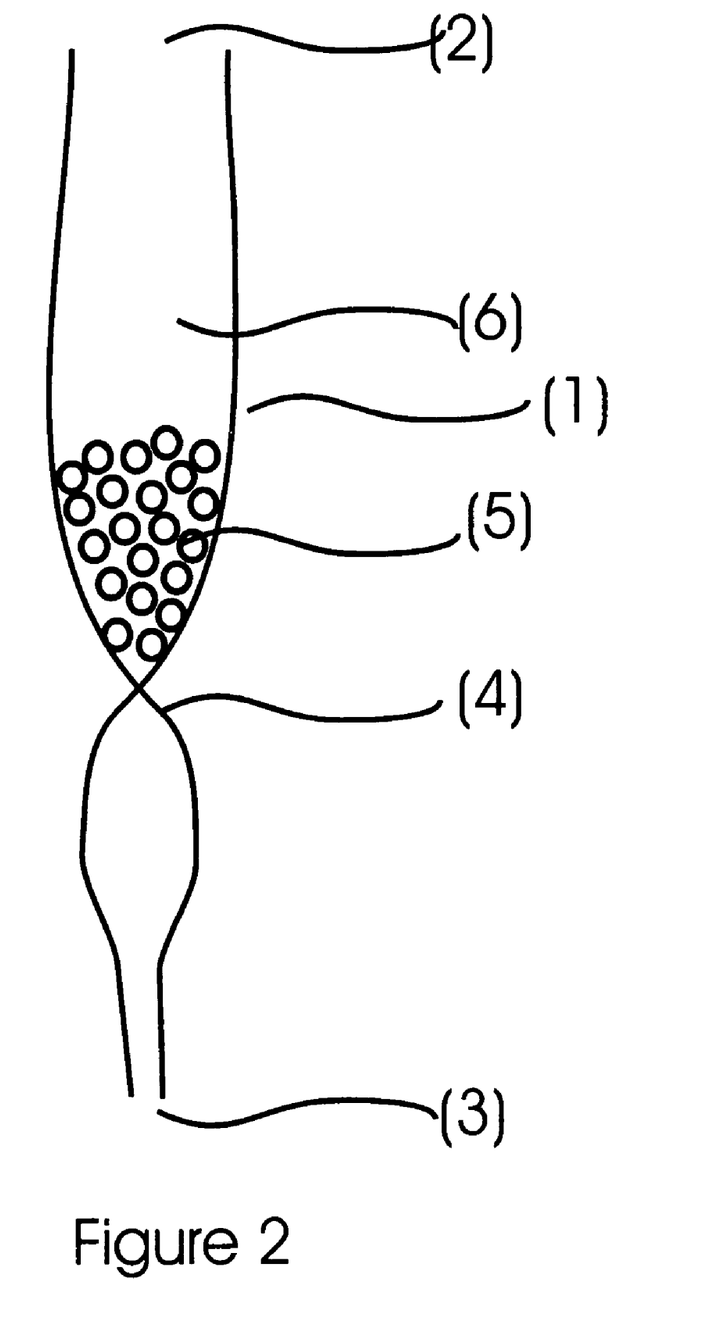
FIG. 2 is an expanded view of one embodiment of the pipette tip, according to the present invention, containing a chromatography material within it.

FIG. 2 is an expanded view of one embodiment of the pipette tip (1), according to the present invention, containing a chromatography material (5) within it. FIG. 2 also shows a sample (6) being placed on top of the chromatographic material (5). Said chromatography material can consist of one or more different types of chromatography or separation materials including, but not limited to, chromatographic silica, affinity, IMAC, polystyrene, carbon, polymers, media, gels, bacteria, living cells, solid powders or any other media used for the purposes of sample filtration, separation or purification. The chromatographic material (5) can also be composed of non-silica, polymer-based, active charcoal, zirconium, titanium, metal oxide, non-metal oxide or other materials. The chromatographic material can be present in a tube (1) in loose form or packed between two narrow spiral openings. In tube (1), chromatographic material can be either in a loose form or packed between a narrow spiral opening at the lower end and a filter disk at the top of the chromatographic media bed.

The said narrow spiral opening can be made while containing the chromatographic media in tube (1), in such a way that the media fixed on the inner surface of the pipette tip or tube (1) in the area of spiral (4) acts like a filter to retain the loose chromatographic media.

Figure 3:
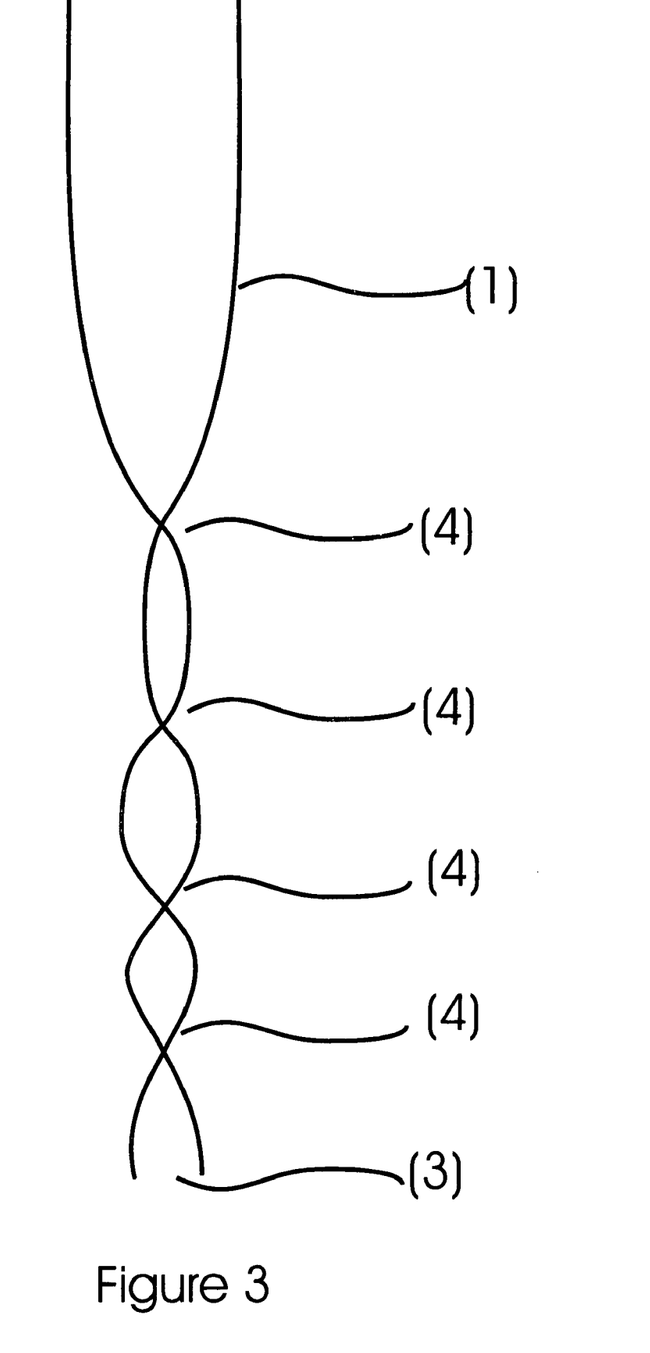
FIG. 3 is an expanded view of one embodiment of the pipette tip (tube), according to the present invention, containing multiple narrow spiral opening.

The said pipette tip has more than one narrow spiral openings FIG. (3) in the tip in a series to hold different chromatographic materials in different compartments that are formed due to multiple narrow spiral openings within the same pipette tip.

Figure 4:
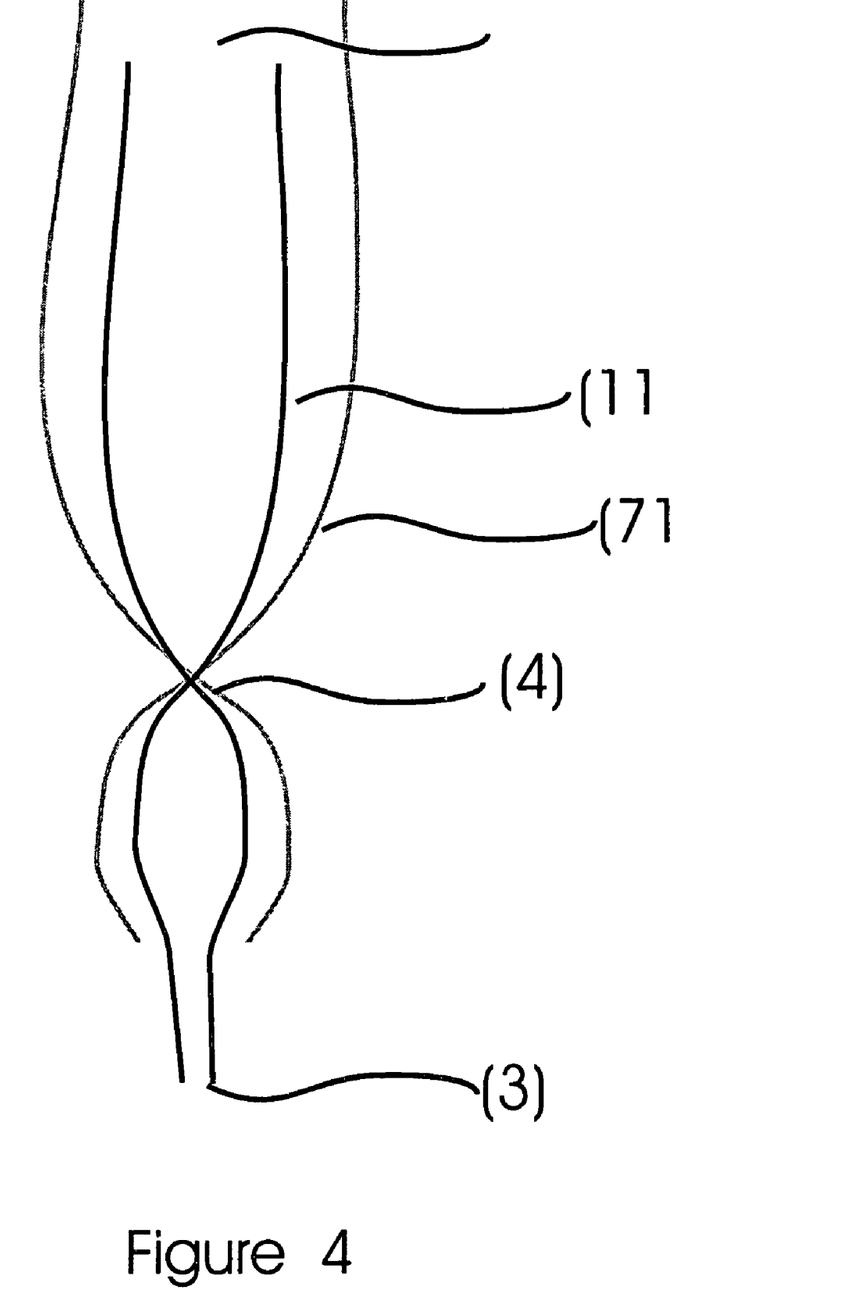
FIG. 4 is an expanded view of one embodiment of a tube containing second tube to strengthen the twist.

Pipette tip (tube) which has an upper end and a lower end and which has a narrow spiral opening at the lower end to permit the selective passage of smaller particles or fluids through said narrow spiral opening while retaining larger particles then the opening in the tip for the sample preparation, said narrow spiral opening can be strengthened (FIG. 4) by placing the said tube in a second tube (7) and twisting both tubes together.

Figure 5:
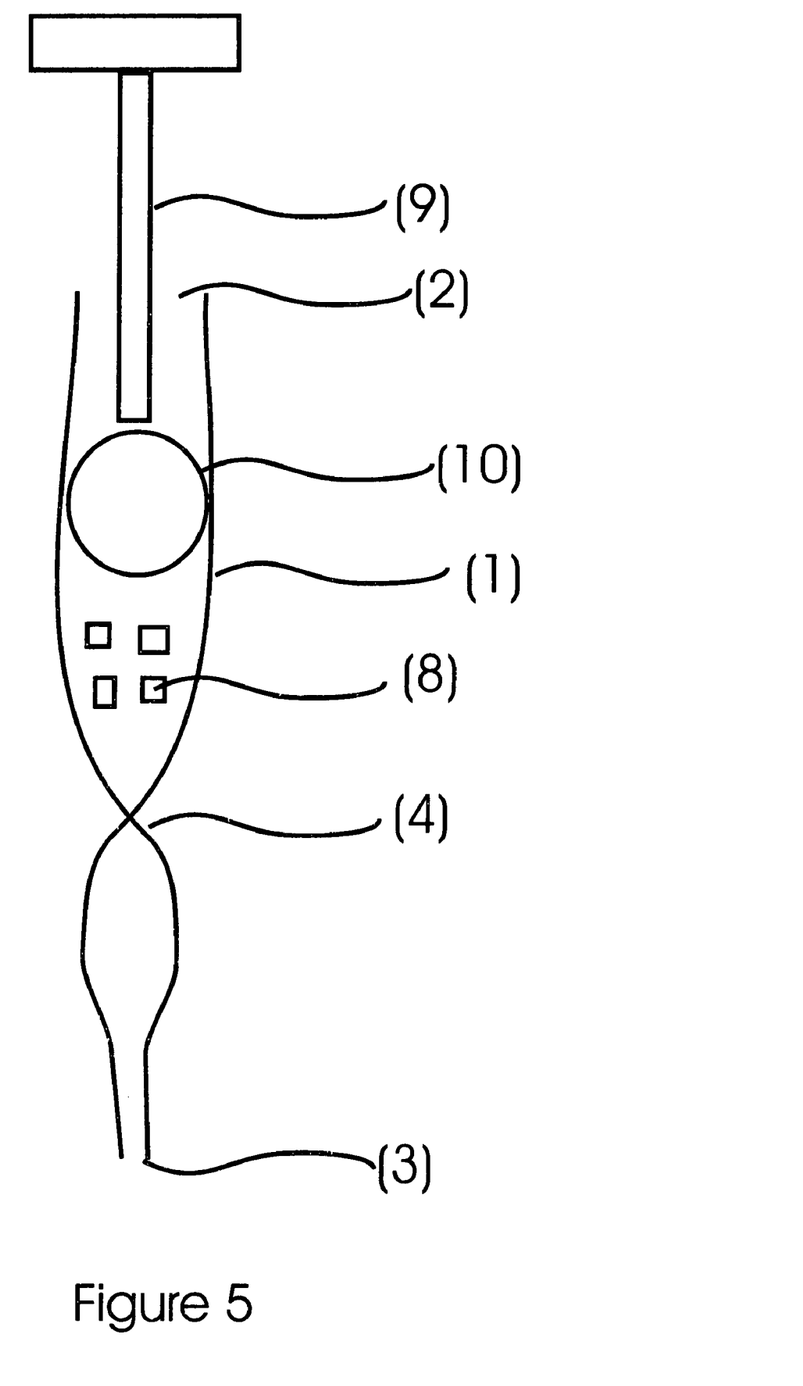
FIG. 5. is expanded view of one embodiment of pipette tip (tube) containing a electrophoresis gel piece and a piston and ball to crush the gel.

In FIG. (5) the pipette tip (tube) which has an upper end and a lower end and which has a narrow spiral opening or a slit at the lower end to permit the electrophoresis gel (8) piece to pass through the narrow spiral opening to be crushed in small pieces. The said electrophoresis gel can be crushed by applying the piston (9), a ball with piston (10), applying the pressure, centrifugation, vacuum or combination thereof. The ball can be either free form or attached to the piston. The diameter of the ball is equal to the inner diameter of the tube or the ball is of such a dimension that it pushes the gel through the narrow spiral opening, but does not come out from the end where the pressure is applied. The ball (10) can be made of any material such as polymer, metal or any inert material. When the piston pushes the gel piece, the ball will crush the gel and due to the applied force on the ball, the gel will pass through the narrow spiral opening and will come out of the tube or pipette tip in small pieces. The size of small pieces will depend on the size of the narrow spiral opening. Furthermore, the piston itself can be of such a form or shape that it can crush the gel and push the small pieces through the narrow spiral opening.

The chromatography material (5) can also be a mix of materials with different particle sizes or different types of materials such as cation and anion exchange materials, affinity materials, and normal phase or reverse phase materials. Said chromatography or separation material (5) can be in any shape or form including but not limited to particle form, powder form, or in any other physical configuration suited to the design of the pipette tip and the experimental conditions. Furthermore, the particles of said chromatographic or separation material (5) can be chemically or physically modified and may be porous or non-porous. The size of the chromatographic material particles can be from nanometers to micrometers.

The chromatography material particles (5) are of such a shape and size that they will not be able to pass through the narrow spiral opening (4) in said pipette tip (1). The particles can be larger in the size then the size of narrow spiral opening. Thus, during the process of sample separation performed by centrifugation, gravitation, vacuum suction, pressure application or by syringe-based sample delivery through the container described herein, the chromatography or separation material is retained in the container. Any other applicable methods can also be used to perform sample preparation and separation. The tube (1) which could be a capillary or tube and has the narrow spiral opening at one end or at both the ends can be used as HPLC column.

The narrow spiral opening (4) can be made at the said lower end (3) of the said pipette tip (1). The narrow spiral opening (4) can be formed by twisting the lower end (3) of the tip (1) in such a way that it does not totally close the opening (3). But the twisting will narrow the opening in such a way that the fluid and small particles can pass through. The twisting can be performed by applying physical pressure, heat or combination of both. The narrow spiral opening can be straight or at an angle.

The narrow spiral opening (4) may be of any shape or size, depending on the specifications of the tube, but is of such dimensions so as to permit the selective passage of materials through the lower end (3) of said pipette tip (1). Said tube (1) is of a volume between 0.0001 and 100 milliliters. The size or diameter of the spiral opening can be from 0.0001-10 mm. The length of the spiral can be from 0.001-1000 mm. The narrow spiral opening can be formed by twisting the tip or tube from 1-360-degree angles. Furthermore, the twisting can be one round (360-degree) or more including multiple rounds of twisting. One round of twisting means that the tip's outer wall is fixed at one end and other end is twisted by 360-degree (one whole round). Furthermore; the narrow spiral opening (4) can also be made during the molding process during which the pipette tip (1) is manufactured.

The passage of the sample through the pipette tip (1) can be performed using any relevant methods, including but not limited to, centrifugation, gravitation, vacuum suction, pressure application or syringe-based sample delivery through the container. The sample components passed through the narrow spiral opening (4) of the pipette tip (1) can be collected in any sample collection tube.

Said tube (1) can be arranged in multiple units of the pipette tip or tube (1), joined together in a 96-tube format. Multiple units of said pipette tips (1) can be joined together to develop a system for the simultaneous preparation of multiple samples. Said pipette tips (1) can be joined together in any type of configuration including but not limited to 2-unit, 8-unit, 48-unit, 96-unit, 384-unit or 1536-unit formats. The pipette tip (1) is either a single unit or a multi-unit system and can be combined with a piston or similar device designed to pull the sample into the tip or push the sample out of the tip.

Figure 6:
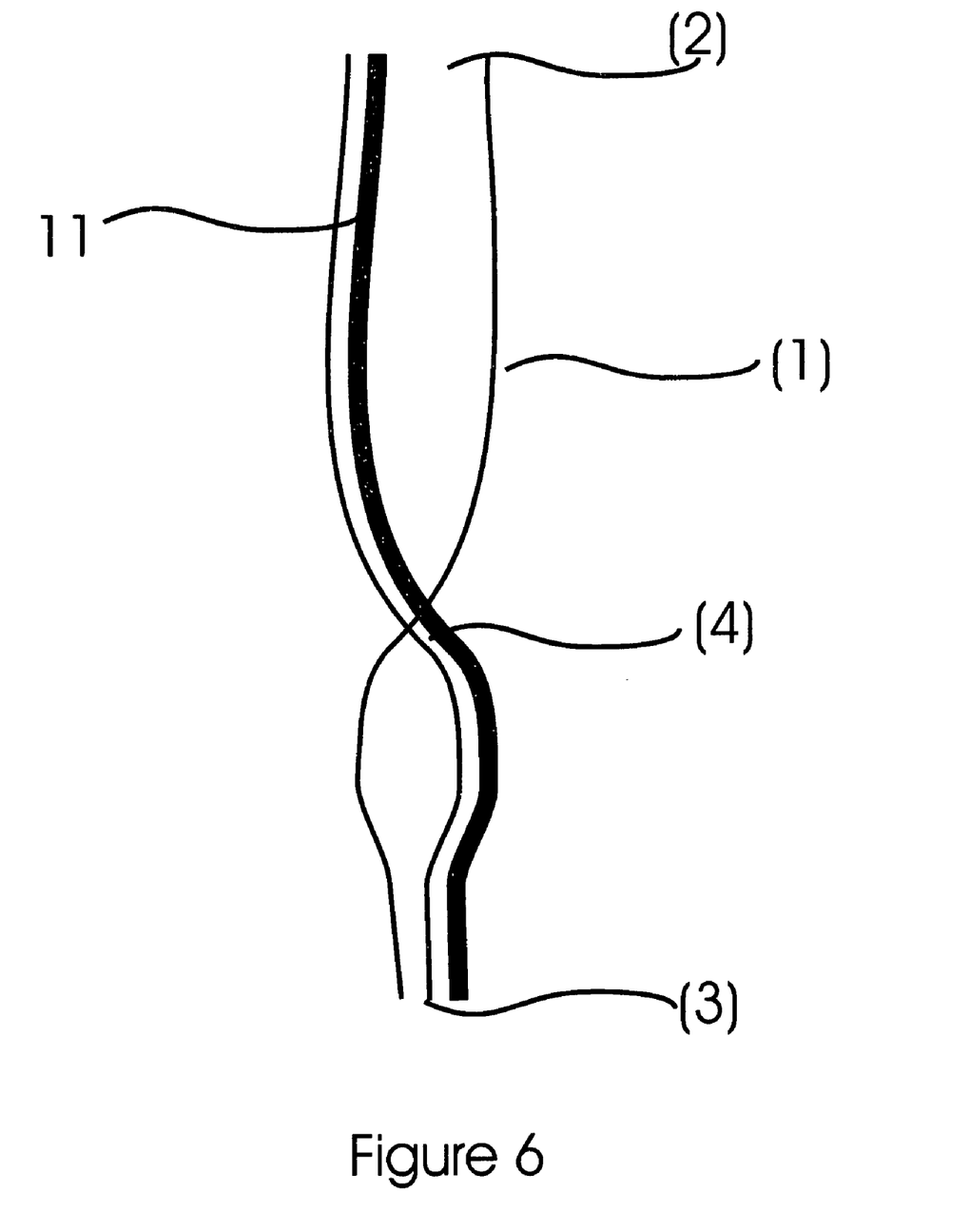
FIG. 6 is expended view of one embodiment of tube containing wire to strength the twist.

In FIG. 6. the tube (1) contains said narrow spiral opening is strengthened by attaching a support such as wire (11) inside or out side of said tube, and said support and said tube are twisted both together to keep the twist angle in position, and the said wire is made of porous, solid or any suitable material.

Figure 7:
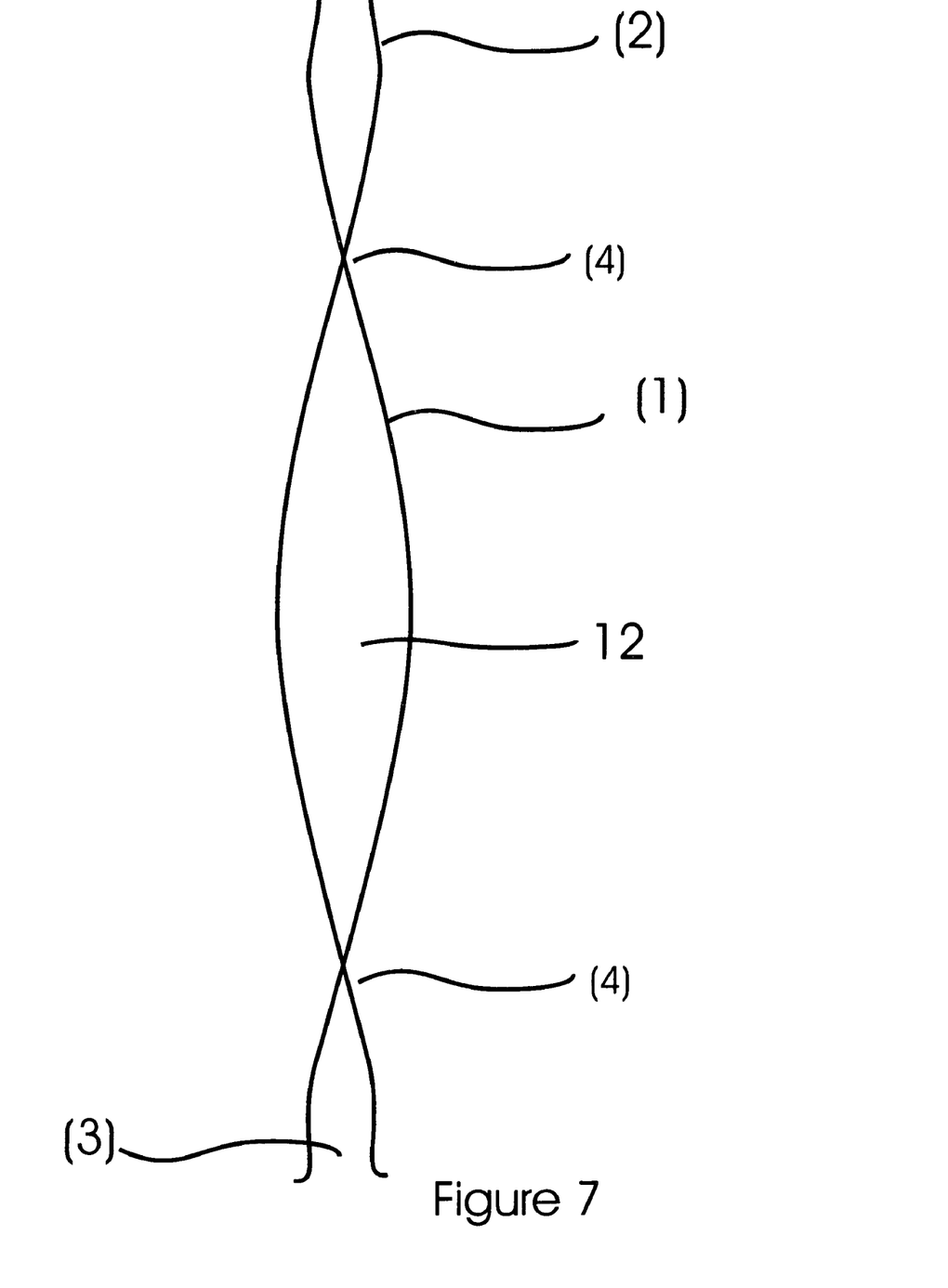
FIG. 7 is an expanded view of one embodiment of a tube where particles are retained loose between two narrow spiral openings.

Said tube (1) contains FIG. 7 said particles are retained loose in the said tube (capillary) between the two said narrow spiral openings (12) for the sample preparation, and said tube can be used as a HPLC column for separation.

Figure 8:
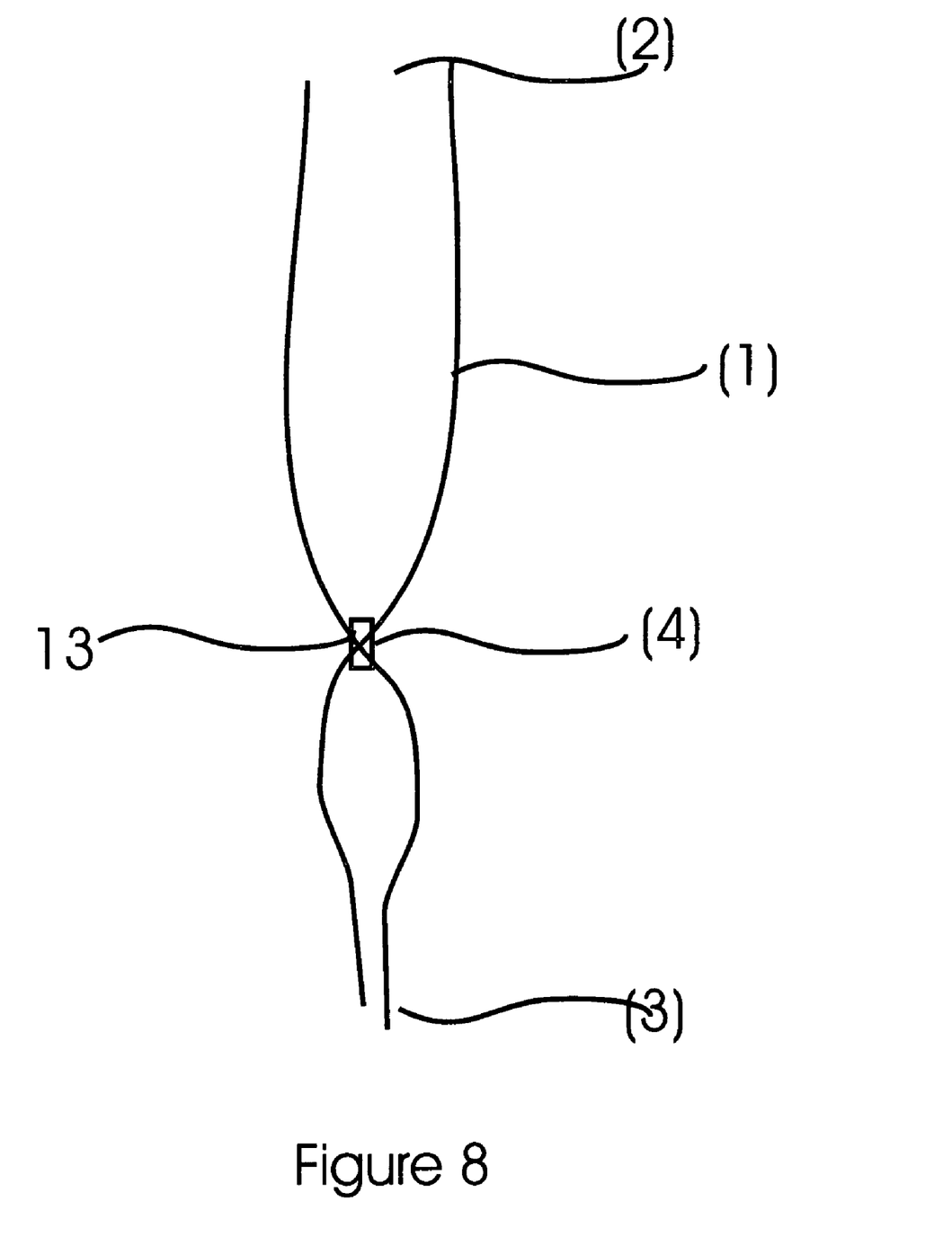
FIG. 8 is an expanded view of one embodiment of a tube where the narrow spiral opening region contains a porous material which acts as a filter to retain chromatographic particles inside the tube.

In FIG. 8. tube which has an upper end and a lower end and the said lower end is twisted to create a narrow spiral opening, the said narrow spiral opening region contains a porous material (13), which act as a filter to retain the chromatographic particle inside the tube. This also helps to hold the filter (13) in place, during the sample pressure under pressure or vacuum.

The pipette tip (tube) described in the present invention has many small sample preparation, filtration and purification applications including but not limited to the purification of DNA, proteins, peptides, lipids, carbohydrates, vitamins and other chemicals and bio-molecules. Separation of sample components can be based on size, chemical properties or physical properties of the sample's component molecules and particles. Samples purified by these methods can be used for further analysis, through mass spectrometry, High Performance Liquid Chromatography (HPLC), electrophoresis, capillary electrophoresis, NMR, enzyme assays, protein binding assays and other chemical or biochemical reactions.

The broader usefulness of the invention may be illustrated by the following examples.

Example #1

Use of the Present Invention for Peptide Sample Preparation

In this instance, a 10-200 micro-liter micro pipette tip is used. By fixing the lower end (3) in clamp, the upper end is twisted in such a way that it is not totally closed. The narrow spiral opening is tested by passing the air through it. A 50 micro-liter slurry of C-18 column material (with particle sizes of 40-60 microns) was introduced into the tip through the top open end (2). The tip was attached to a pipette and pressure was applied through the pipette. The column material settled at the bottom of the pipette tip while the water flowed through the spiral opening at the lower end.

A 20 micro-liter peptide solution containing buffer was pipetted on top of the C-18 column material bed in the pipette tip. Pressure was applied through the pipette and the sample fraction passing through the lower end of the tip was collected in a separate tube. The peptide was retained in the tip while water and impurities passed through the spiral opening at the lower end. The column was washed with 20 micro-liters of water a few times and the peptide was then eluted from the column using 50 percent isopropanol. The purified peptide sample was then analyzed by HPLC.

While a specific embodiment of the invention has been shown and described in detail to illustrate the application of the principles of the invention, it is understood that the invention may be embodied otherwise without departing from such principles and that various modifications, alternate constructions, and equivalents will occur to those skilled in the area given the benefit of this disclosure and the embodiment described herein, as defined by the appended claims.

What is claimed is:

1. A tube for sample preparation that has two ends and the said tube contains chromatographic particles between the two ends and at least one end is twisted in such a way as to create a narrow spiral opening at the said end to permit the selective passage of the fluids through the said narrow spiral opening while retaining said particles larger than the said spiral opening in the said tube.

2. A tube as in claim 1, wherein said tube is selected from the group including but not limited to tube, capillary, tip, housing, column, and tapered column; and, combination thereof.

3. A tube, as in claim 1, wherein said tube is of any shape or size.

4. A tube as in claim 1, wherein multiple units of said tube are joined together in any type of configuration including but not limited to 2-unit, 8-unit, 48-unit, 96-unit, 384-unit or 1536-unit formats.

5. A tube as in claim 1, wherein the said tube is of a volume between 0.0001 and 100 milliliters, and the length of said tube is between 0.1-1000 mm, and internal diameter of the said tube is between 0.0001-25 mm.

6. A tube as in claim 1, wherein the said narrow spiral opening is created by a process selected from the group including but not limited to a chemical, physical, mechanical, thermal, pressure, during molding, during extruding of the said tube; and, combination thereof.

7. A tube as in claim 1, wherein the said narrow spiral opening is created by keeping one end fixed while rotating the other end of the said tube at an angle ranging between 1 to 360-degree rotation or multiples thereof.

8. A tube as in claim 1, wherein the said narrow spiral opening exists at any place between the two ends.

9. A tube as in claim 1, wherein the said tube can have one or more (twists) spirals at different places along the tube to hold different chromatographic materials in different compartments formed due to multiple twists in the said tube.

10. A tube as in claim 1, wherein said narrow spiral opening can be strengthened by placing the said tube inside a second tube and twisting both tubes together.

11. A tube as in claim 1, wherein said narrow spiral opening is strengthened by attaching a support such as wire inside or out side of said tube, and said support and said tube are twisted both together to keep the twist angle in position, and the said wire is made of porous, solid or any suitable material.

12. A tube as in claim 1, wherein said particles are retained loose in the said tube (capillary) between the two said narrow spiral openings for the sample preparation, and said tube can be used as a HPLC column for separation.

13. A tube which has an upper end and a lower end and the said lower end is twisted to create a narrow spiral opening, the said narrow spiral opening region contains a porous material, which act as a filter and retains chromatographic particles inside the tube.

* * * * *